US005115457A

United States Patent [19]

Lewandowski et al.

[11] Patent Number: 5,115,457
[45] Date of Patent: May 19, 1992

[54] METHOD OF DETERMINING TITANIUM DIOXIDE CONTENT IN PAINT

[75] Inventors: B. Pinkerton Lewandowski, Wilmington, Del.; Michael J. Fahsel, Pennsville, N.J.

[73] Assignee: E. I. Du Pont de Nemours and Company, Wilmington, Del.

[21] Appl. No.: 591,122

[22] Filed: Oct. 1, 1990

[51] Int. Cl.$^5$ .......................................... G01N 23/223
[52] U.S. Cl. ....................................... 378/45; 378/48; 378/88; 378/53
[58] Field of Search ................ 378/127, 129, 143, 144, 378/45, 46, 50, 53, 90, 44, 48.88, 45

[56] References Cited

U.S. PATENT DOCUMENTS

| | | | |
|---|---|---|---|
| 4,344,181 | 8/1982 | Baecklund | 378/45 |
| 4,461,017 | 7/1984 | Koga et al. | 378/44 |
| 4,680,716 | 7/1987 | Naudi | 378/44 |
| 4,696,023 | 9/1987 | Kuusi | 378/46 |
| 5,020,084 | 5/1991 | Robertson | 378/46 |

OTHER PUBLICATIONS

Andrews, C. R. and R. K. Mays, "Instrumental Techniques for the Analysis of Paper Fillers and Pigments", *Adv. X-Ray Anal.*, vol. 22 (1979), pp. 207-212.

Kobayashi, Y. et al., "A Glass Bead Fluorescent X-Ray Method for Analysis of Samples Whose Main Component is Silicic Acid", *Kagaku Gijutsu Kenkyusho Hokuku*, vol. 78, No. 7 (1983), pp. 365-368.

Lewis, Peter A., ed., *Pigment Handbook, Volume 1: Properties and Economics*, 2nd ed., John Wiley & Sons, Inc.: New York, 1988, pp. 1-41.

"Designation: D 4563-86, Standard Test Method for Determination of Atomic Absorption Spectroscopy of Titanium Dioxide Content of Pigments Recovered from Whole Paint", 1986, pp. 1069-1073.

*Primary Examiner*—Janice A. Howell
*Assistant Examiner*—Kim-Kwok Chu
*Attorney, Agent, or Firm*—David J. Gould

[57] ABSTRACT

The amount by weight of TiO2 per gallon of paint in a paint sample is determined by X-ray fluorescence spectroscopy. The sample is prepared by weighing a portion of the sample while wet and then drying the sample. The dried sample is then calcined to produce an ash residue, which is weighed. The ash residue is then ground and heated to drive off any remaining moisture before being fused with a flux material into a glass bead. The amount of TiO2 in the fused glass bead is determined by an X-ray fluorescence instrument which has been previously calibrated with similar fused glass beads having known amounts of TiO2. The quantitative result of the X-ray fluorescence determination is then extrapolated back to determine the pounds of TiO2 per gallon of paint.

11 Claims, No Drawings

METHOD OF DETERMINING TITANIUM DIOXIDE CONTENT IN PAINT

BACKGROUND OF THE INVENTION

This invention relates to methods of determining the titanium dioxide content in paint. More particularly, this invention relates to a method of determining the titanium dioxide content in paint by X-ray fluorescence spectroscopy.

Titanium dioxide (TiO2) is an important component of modern latex and solvent paints and is used in various quantities to control the opacity. (See R.R. Blakey et al., *Pigment Handbook*, Vol. I-A-a, "Titanium Dioxide", Wiley & Sons, New York (1988). The opacity of a wet paint is a factor in determining the spread rate or area of coverage per gallon of paint. During 1989 in the United States, in architectural paints alone, 335,000 tons of titanium dioxide were used. Often, it is desired to know the TiO2 content of a particular paint, e.g., in market studies, chemical studies, etc. Since paint manufacturers often do not include titanium dioxide content on the can label analysis, this information is no longer readily available.

To improve performance in finished goods, commercial TiO2 pigments are frequently treated with inorganic oxides such as alumina and silica. Treated TiO2 has the inorganic oxides precipitated onto the surface of the TiO2 pigment particles so as to improve pigment spacing for improved optical properties as well as improved dispersability and durability. "Pure TiO2" is TiO2 with no surface treatment which is greater than 97% pure in TiO2 content.

One prior art approach for determining the titanium dioxide content in paint is atomic absorption analysis utilizing a spectrometer (see "Determination by Atomic Absorption Spectroscopy of Titanium Dioxide Content of Pigments Recovered from Whole Paint, " *Annual Book of ASTM Standards*, 1986, 1069–1073). This approach, however, is most applicable to quality control situations, wherein the same type of product is repeatedly analyzed. There is an additional problem with the atomic absorption spectroscopy approach in that it is difficult to dissolve samples of paint pigments into the solution used in performing the analysis. Difficulty in dissolving the paint samples often results in only a small sample being used. Since relatively large volumes of paint cannot be used for analysis, rapidly achieving high precision determinations of the TiO2 content is very difficult using this approach.

In view of the aforementioned considerations, there is a need for a more satisfactory method of determining titanium dioxide content in commercial paints.

SUMMARY OF THE INVENTION

This invention provides a new and improved method of determining the titanium dioxide content in paint. The instant invention contemplates reducing a sample of paint to ash and quantitatively analyzing the ash by X-ray fluorescence spectroscopy.

In accordance with a preferred embodiment of the invention, prior to analysis by X-ray fluorescence spectroscopy, ash samples are prepared as glass beads by fusion with glass flux and then analyzed by an X-ray fluorescence spectroscopy instrument which has been previously calibrated with standard samples of pure materials fused in a similar manner.

In accordance with a still more specific embodiment of the invention, the paint sample is derived from a quantity of wet paint which is weighed into a tared container and set to dry. The dry sample is then calcined in a muffle furnace to produce the ash sample. The ash sample is then ground in a mortar and pestle or the like, and dried. Preferably, the sample is configured as the glass bead for analysis by fusion with a mixture of in the range of 30% to 70% Na2B4O7 and 30% to 70% Li2B4O7 at an ash sample to flux ratio of approximately 1 part ash to a range of 3 to 20 parts flux. In a preferred embodiment, the flux mixture is approximately 50% Na2B4O7 and approximately 50% Li2B4O7 and the ash sample to flux ratio is 1 part ash to 9 parts flux. Other flux combinations containing LiBO2 may also be used.

The results of the X-ray fluorescence analysis is used to determine the weight-per-unit volume of TiO2 in the paint sample. This parameter can be used, for example, to determine the spread rate or area that the selected volume of the paint sample will cover.

PREFERRED EMBODIMENTS

A. Drying Emulsion Paint

In accordance with a preferred embodiment of the instant invention, a first step in determining the percentage of TiO2 in commercial emulsion paints is to thoroughly mix the paint to be analyzed and then weigh a sample, e.g., no more than about 15 grams of the paint into a tared container.

Weighing the paint follows a conventional procedure wherein a weigh dish such as a Fisherbrand Aluminum Weigh Dish 08-732 is placed on a four decimal place balance and the weight recorded as the TIN WEIGHT. In a preferred embodiment, no more than 15 grams of the paint, but enough to cover the bottom of the weigh dish, is placed on the weigh dish with an eye dropper. The weigh dish with the sample is then weighed immediately on the four decimal place balance to determine the SAMPLE TIN WEIGHT. The WET PAINT SAMPLE WEIGHT is then determined by subtracting the TIN WEIGHT from the SAMPLE TIN WEIGHT. The sample is initially dried by placing the tared container and sample in an oven, e.g., set at 100° C. for approximately 8–12 hours. The tared container is removed from the oven, cooled in a desiccator to room temperature and then weighed to determine the DRY PAINT SAMPLE TIN WEIGHT. The DRY PAINT WEIGHT is then determined by subtracting TIN WEIGHT from the DRY PAINT SAMPLE TIN WEIGHT. In order to determine the percent WEIGHT SOLIDS of wet paint, the DRY PAINT WEIGHT is divided by the WET PAINT WEIGHT. The dried sample is then ready for ashing, the procedure for which will be explained in detail hereinafter.

B. Drying Alkyd Paint

The alkyd paint sample is thoroughly mixed and a description of the sample is marked on the back of a Q panel #A412. The marked panel is then placed on a three place balance and the weight is recorded as PANEL WEIGHT. The panel is then removed and placed on a vacuum plate. The feet of a 0.0025 inch clearance draw down blade, e.g., a Bird Applicator, are taped with scotch tape to reduce friction of metal to metal contact when making the drawn down. The alkyd paint sample is placed on the top upper portion of the panel and the paint sample is drawn down with the draw down blade. The panel is then removed from the vacuum plate placed on a balance to record the PANEL PAINT WEIGHT. The panel weight is subtracted from the PANEL PAINT WEIGHT to determine the SAMPLE WEIGHT.

The panel is then placed on a wire drying rack and the drying rack placed in an explosion proof oven set at 100° C. for about 8-12 hours. The wire rack is then removed from the oven and cooled for about 5 minutes to a safe handling temperature. It is important that time and open air be minimized in order to avoid attraction of moisture which may alter weight. The panel is then placed on a three place balance and weighed to record the PANEL DRY PAINT WEIGH from which the panel weight is subtracted to determine the DRY PAINT WEIGHT. In order to determine the paint weight solids of wet paint, the DRY PAINT WEIGHT is divided by the SAMPLE WEIGHT and multiplied by 100.

C. Ashing of Both Emulsion Paint and Alkyd Paint Samples

A Coors ceramic crucible #60108 is marked with the sample to be ashed. The crucible is placed on a four decimal place balance and the weight is recorded as the CRUCIBLE WEIGHT. The crucible is removed from the balance, the sample is placed into the crucible, both are reweighed, and the crucible sample weight is reported. With emulsion paints, the sample is simply the dried paint from the solids determination. Since alkyd-type paint weight solids are determined by the draw down method, another approach must be followed in which the alkyd paint, approximately 15 grams thereof, is poured directly into the pre-weighed crucible. The crucible is placed in an explosion proof oven overnight at 100° C. Prior to the ashing in a muffle furnace, the "skim-over" is ruptured, but none of the sample is removed.

With either the emulsion paints or alkyd paints, the muffle furnace is maintained in a range of 800°-1200° C. and preferably set at 900° C. for a period in range of 1 to 4 hours and preferably about 2 hours. The crucible containing the sample is placed in the muffle furnace oven with the door closed slightly, but not shut completely, if the muffle furnace does not have internal ventilation. Soot may be created as the ashing step begins and one should wait until soot from previous samples stops before placing a second sample into the oven. When all samples are in the muffle oven and stabilized, the door should be tightly shut. After the oven temperature again reaches 900° C., the sample should be left in the oven for two hours at 900° C.

The samples are then moved from the oven and placed on an insulated area for approximately 10 minutes and thereafter placed in a desiccator. A lid is placed on the desiccator and after a few minutes opened to release possible heat build up. The samples are then left in the desiccator for another 20 minutes.

The crucible with the ash therein is weighed to determine the CRUCIBLE ASH WEIGHT. The contents of the crucible is then entered into an appropriately labelled two-ounce screw top jar and the CRUCIBLE WEIGHT is subtracted from the CRUCIBLE ASH WEIGHT to determine the ASH WEIGHT. To determine the percent ash, the ASH WEIGHT is divided by the SAMPLE WEIGHT and multiplied by 100.

Specifically for alkyd paint, the percentage ash is determined by weighing the crucible with a wet paint sample and subtracting the crucible weight therefrom to determine the WET PAINT SAMPLE WEIGHT. The wet paint sample weight is multiplied by the percent solids of alkyd paint to determine the dry sample weight. Thereafter, the ASH WEIGHT is divided by the DRY SAMPLE WEIGHT and multiplied by 100 to determine the percent ash.

D. Grinding Procedures for Ash Paint Samples

The entire grinding procedure should be done in a hood to avoid dust inhalation. A Spex tungsten-carbide vial is used which has two open ends. One end is closed by a screw-on cap with a corprene gasket between the vial and lid and the ashed paint sample is emptied into the vial. Four 7/16" tungsten carbide balls are then placed in the vial and a corprene gasket and screw-on cap placed on the other end and sealed. Up to four of the vials are positioned in wooden platform holders and placed in a shaker, such as a RED DEVIL SHAKER, and shaken for 15 minutes. The contents of each vial is then emptied onto a weighing paper and the balls are removed from the sample. The sample contents from the weighing paper are then placed in two ounce glass vials properly marked to identify the sample. The glass vials and balls are then thoroughly cleaned to remove any residue from the grinding step so as to not contaminate samples ground in subsequent tests.

E. The Fusing Step

The ground ash is then preferably dried for approximately two hours at 100° C. and configured as a glass bead, e.g., in the form of a disk. Preferably this is accomplished by fusion with a flux material of 30% to 70% $Na_2B_4O_7$ and 30% to 70% $Li_2B_4O_7$ at a ratio in the range of 1 part ash to a range of 3 to 20 parts flux. The selected range of the mixture of $Na_2B_4O_7$ and $Li_2B_4O_7$ is necessary to dissolve high $TiO_2$ content pigment. A preferred flux material is a mixture of approximately one-half $Na_2B_4O_7$ and approximately one-half $Li_2B_4O_7$, which is mixed at a sample-to-flux ratio of approximately 1 part ash to 9 parts flux. The ratio of flux to sample is critical in that while higher ratios make it easier to dissolve the sample, lower final $TiO_2$ content in the pellet makes it difficult to match the pellets with analytical procedures developed for XRF analysis.

Fusion can be accomplished, e.g., by heating the mixture, e.g., at 1500°C. for 10 minutes or equivalent conventional conditions, e.g., 1000°-1600° C. for 5-30 minutes. Regarding the fusion step, see, e.g., Claisse, F., Norelco Reporter, 4, 3-17, 17, 19, 20 (1957), Province of Quebec, Canada, Dept. Mines, 1956; Longobucco, R., Anal. Chem., 34, 1263-1267 (1962); and Jenkins, R., "An Introduction to X-ray Spectrometry", Heyden, New York, 1974, pp. 137, 138.

The resulting fused glass bead is analyzed by X-ray fluorescence spectroscopy (XRF) using techniques standard per se. For example, a Philips Model 1480 XRF instrument can be used with an X-ray analysis program known to applicant's assignee as COMBORE, which relies on the specific aforementioned parameters of a 1/9 standard sample to flux ratio, 50% $Na_2B_4O_7$ and 50% $Li_2B_4O_7$ flux mixture and a 1500°C. fusion temperature. The XRF instrument can be calibrated utilizing a series of standard samples made from components, including relatively pure titanium dioxide, silicon dioxide, aluminum oxide, and calcium carbonate which have been fused in a manner identical to the sample under scrutiny and under XRF conditions identical to those used in the known sample analysis. A calibration curve can be constructed conventionally if desired.

X-ray lines which can be used include the Ti K alpha at 4.49 Kev and the K beta at 4.91 Kev. Fluorescent wavelengths of Ti suitable for monitoring are 2.7497A, 2.5139A.

The percentage of pure titanium dioxide in each ash sample is provided by the X-ray fluorescence spectroscopy and is used to determine both the percentage of pure TiO2 in wet paint and the percentage of surface treated titanium dioxide wet paint.

F. Calculations From Notes Taken During the Aforedescribed Procedures

The following information is available for each sample:

1. Ash Weight
2. Percentage Ash
3. Percentage Solids of Wet Paint
4. Gallon Weight of Wet Paint
5. Percentage Pure Titanium Dioxide in Ash as Determined by XRF.

Using the above parameters, the following calculations are made:

$$\text{Dry sample weight} = \frac{\text{Ash Weight}}{\% \text{ Ash}}$$

$$\text{Grams of Wet Paint (used for ashing)} = \frac{\text{Dry Sample Weight}}{\% \text{ Solids of Wet Paint}}$$

$$\frac{\text{Grams of Element}}{\text{in Wet Paint}} = \frac{\text{Ash Weight} \times \% \text{ of Ash Pure Element}}{\text{by X-Ray}}$$

$$\% \text{ of Pure Element in Wet Paint} = \frac{\text{Grams of Element}}{\text{Grams of Wet Paint}} \times 100$$

To break down into surface treated TiO$_2$ (instead of "pure" TiO$_2$)

$$\text{Grams of "pure" TiO}_2 \text{ in Wet Paint} = \frac{\text{Ash Weight} \times \% \text{ of}}{\text{Ash Pure TiO}_2 \text{ by X-Ray}}$$

$$\frac{\text{Grams of Surface Treated}}{\text{TiO}_2 \text{ in Wet Paint}} = \frac{\text{Grams of "pure" TiO}_2 \text{ in Wet Paint}}{\% \text{ TiO}_2}$$

$$\frac{\% \text{ Surface}}{\text{Treated TiO}_2 =} \frac{\text{Grams of Surface Treated TiO}_2 \text{ in Wet Paint}}{\text{Grams of Wet Paint}} \times 100$$

$$\frac{\text{Pounds of Surface}}{\text{Treated TiO}_2 \text{ per gallon}} = \frac{\text{Gallon Weight of Paint} \times \% \text{ Surface}}{\text{Treated TiO}_2 \text{ in Wet Paint}}$$

FOR THE PURPOSE OF THIS METHOD: PURE TiO2 means TiO2 without any treatment.

SURFACE TREATED TiO2 takes surface treatment into consideration.

G. Calculation for Lotus Program

1. Column A—Code—abbreviation of manufacturer (i.e., SB=Standard Brands) and sample number
2. Column B—Description—Brand name on paint can (i.e., Acrylic Semi-Gloss)
3. Column C—Ash Weight—grams calculation from ashing sample
4. Column D—% Ash—percent calculated from ashing sample
5. Column E—Dry Sample Weight—calculated from columns C & D
6. Column F—% Solids of Wet Paint—calculated from solids determination
7. Column G—Grams of Wet Paint—calculated from columns E & F
8. Column H—% of Ash Pure TiO2 by X-Ray
9. Column I—Grams Pure TiO2 —in Wet Paint—calculated from column C & H
10. Column J—% Pure TiO2 —calculated from columns I & G
11. Column K—Type—customer contact information
12. Column L—% TiO2 —product information bulletin
13. Column M—Grams of Surface Treated TiO2 in Wet Paint—calculated from columns I & L
14. Column N—% Surface Treated TiO2 in Wet Paint—calculated from columns M & G
15. Column 0 —Gallon Weight of Wet Paint—calculated using gallon weight cup
6. Column P—Pounds of Surface Treated TiO2 in a Gallon of Commercial Paint—calculated from columns 0 & N

WRITTEN CALCULATIONS OF LOTUS PROGRAM

COLUMN E—+C/D*100
COLUMN G—+E/F*100
COLUMN I—+C*H/100
COLUMN J—+I/G*100
COLUMN M—+I/L*100
COLUMN N—+M/G*100
COLUMN P—+O*N/100

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

In the foregoing and in the following example, all temperatures are set forth uncorrected in degrees Celsius; and, unless otherwise indicated, all parts and percentages are by weight.

The entire disclosures of all applications, patents and publications, cited above and below, are hereby incorporated by reference.

EXAMPLE

It has been found that the aforedescribed approach provides a very accurate determination of the amount of TiO2 in a sample. The following tests were conducted utilizing first a single technician and then five technicians (to show the reliability of the invention). The results are set forth as an average analysis, a standard deviation, and a 95% confidence limit.

Experimental Details

For each sample, the following procedure was used:

Precision—Single Operator

TFW means "testing formula white" paint R-900 and R-931 are grades of titanium dioxide.

The following was calculated from eight replicate analyses of one sample performed by one technician over a period of eight days. The average analysis ($\bar{X}$), standard deviation (S), and 95% confidence limits (95% CL) established by a single operator are as follows:

| Sample | $\bar{x}$ in pounds of TiO2/Gallon | S | 95% CL |
|---|---|---|---|
| TFW 178 R-900 | 1.55 | 0.005 | ±0.012 |

Precision - Multiple Operator

Twenty replicate analyses of each sample performed by five technicians over a period of four days (four days for each sample) gave the following average analysis ($\bar{X}$), standard deviation (S), and 95% confidence limits (95% CL):

| Sample | $\bar{x}$ in pounds of TiO2/Gallon | S | 95% CL |
|---|---|---|---|
| TFW 178 R-900 | 1.59 | 0.013 | ±0.026 |
| TFW 178 R-931 | 1.58 | 0.011 | ±0.022 |
| TFW 182 R-900 | 2.38 | 0.043 | ±0.086 |
| TFW 182 R-931 | 2.39 | 0.014 | ±0.030 |

Accuracy

The following average analysis and standard deviations were calculated by comparing the predicted formula pounds per gallon of TiO2 versus the experimental test information in the precision section:

| Sample | $\bar{x}$ in pounds of TiO2/Gallon | S |
|---|---|---|
| TFW 178 R-900 | 1.65 | ±0.075 |
| TFW 178 R-931 | 1.64 | ±0.083 |
| TFW 182 R-900 | 2.32 | ±0.095 |
| TFW 182 R-931 | 2.32 | ±0.102 |

In the "Precision - Multiple Operator" section, TFW 178 R-900 had an average analysis of 1.59 pounds of TiO2 per gallon of paint, a standard deviation of 0.013, and a 95% confidence limit of 0.026. In other words, the true value will lie between 1.56 to 1.62 pounds per gallon of TiO2 in the sample gallon of paint.

The preceding example can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method of determining the TiO$_2$ content of a wet paint sample comprising drying the sample, calcining the dried sample to produce an ash sample fusing the ash sample with a flux, analyzing the resultant product by X-ray fluorescence to determine the TiO$_2$ content thereof, and correlating said TiO$_2$ content so determined with said wet paint sample to determine the weight per unit volume of TiO$_2$ in said wet paint sample.

2. The method of claim 1, wherein the sample of wet paint analyzed is approximately 15-100 g which is dried for a period of 8-12 hours at a temperature of from about 100° C. and wherein dry sample is calcined in a muffle furnace set at about 800°-1200° C. for a period of from about 120 minutes.

3. The method of claim 2, wherein the ashed sample is are dried for approximately 2 hours at approximately 110° C., after being ground.

4. The method of claim 2, wherein the wet paint sample is dried at about 100° C. and wherein the dried sample is calcined at about 900° C.

5. The method of claim 4, wherein the ashed sample is dried for approximately 2 hours at approximately 110° C. after being ground.

6. The method of claim 1, wherein the fusion of the dried ash with a flux is performed by mixing the dried ash with Na2B4O7 and Li2B4O7.

7. The method of claim 6, wherein the Na2B4O7 and Li2B4O7 are used in approximately equal amounts, at an ash-to-flux ratio of approximately 1 part ash to 9 parts flux by weight and wherein fusion is accomplished by heating the mixture at approximately 1500° C. for approximately 10 minutes.

8. A method of determining the amount of TiO2 in a paint sample, comprising calcining the sample into a dry ash and fusing the ash with a flux, thereafter determining the amount of TiO2 in the fused product by X-ray fluorescence through comparing fluorescence output with standard samples having a known TiO2 amount and correlating said amount of TiO2 with said sample to determine the weight of TiO2 per unit volume.

9. The method of claim 1 wherein the wet paint from which the sample is obtained is an emulsion paint and wherein the drying step comprises placing no more than about 15 grams of wet paint in a weighed dish and weighing the sample before drying the sample to determine the percentage of solids by dividing the dry paint weight by the wet paint weight.

10. The method of claim 2 wherein the wet paint from which the sample is obtained is an alkyd paint and wherein the drying step comprises pouring the wet alkyd paint sample directly into a pre-weighed crucible used in the calcining step and drying the sample in the crucible.

11. The method of claim 10 wherein a separate portion of the alkyd paint is dried to determine the percent solids therein by drawing down a layer on a panel, drying the layer on the panel and dividing the dry sample weight by the wet sample weight.

* * * * *